United States Patent [19]
Michael et al.

[11] Patent Number: 5,939,080
[45] Date of Patent: *Aug. 17, 1999

[54] HYDROPHOBIC AGENTS AND NON-POLYMERIC SURFACTANTS USE IN ORAL CARE PRODUCTS

[75] Inventors: Daniel Wayne Michael, Maineville; Gregory Berry, Cincinnati; James Grigg Upson, Springdale, all of Ohio

[73] Assignee: The Procter & Gamble Company, Cincinnati, Ohio

[ * ] Notice: This patent issued on a continued prosecution application filed under 37 CFR 1.53(d), and is subject to the twenty year patent term provisions of 35 U.S.C. 154(a)(2).

[21] Appl. No.: 08/781,222

[22] Filed: Jan. 10, 1997

[51] Int. Cl.$^6$ .............................. A61K 6/00; A61K 7/00; A61K 7/16
[52] U.S. Cl. ............................................. 424/401; 424/49
[58] Field of Search ..................... 424/400, 401, 424/52, 404, 49, 43; 252/186; 514/835, 900, 901, 902

[56] References Cited

U.S. PATENT DOCUMENTS

| | | | |
|---|---|---|---|
| 3,928,560 | 12/1975 | Neely et al. | 424/52 |
| 3,988,433 | 10/1976 | Benedict | 424/53 |
| 4,452,820 | 6/1984 | D'Amelia et al. | 426/3 |
| 4,474,750 | 10/1984 | Gaffar et al. | 424/49 |
| 4,627,977 | 12/1986 | Gaffar et al. | 424/52 |
| 4,844,883 | 7/1989 | Patel | 424/49 |
| 5,013,557 | 5/1991 | Tai | 424/493 |
| 5,057,310 | 10/1991 | Hill et al. | 424/52 |
| 5,061,182 | 10/1991 | Kubo et al. | 433/199.1 |
| 5,108,763 | 4/1992 | Chau et al. | 426/5 |
| 5,110,583 | 5/1992 | Sampathkumar | 424/48 |
| 5,167,964 | 12/1992 | Muhammad et al. | 424/482 |
| 5,180,710 | 1/1993 | Naef et al. | 512/26 |
| 5,192,532 | 3/1993 | Guay et al. | 424/53 |
| 5,242,910 | 9/1993 | Damani | 514/152 |
| 5,412,125 | 5/1995 | Philippe | 554/35 |
| 5,445,814 | 8/1995 | Liang | 424/52 |

OTHER PUBLICATIONS

U.S. application No. 08/782,470, Michael et al., filed Jan. 10, 1997.
U.S. application No. 08/782,468, Michael, filed Jan. 10, 1997.

*Primary Examiner*—Thurman K. Page
*Assistant Examiner*—Sharon Howard
*Attorney, Agent, or Firm*—Angela Marie Stone; Betty J. Zea

[57] ABSTRACT

Disclosed are oral compositions and methods for reducing plaque in a human or lower animal subject comprising applying to the teeth of the subject an oral composition comprising one or more hydrophobic solvents having one or more characteristics selected from the group consisting of a hydrogen bonding parameter of less than about 7.0 and a water solubility of less than about 10%; one or more non-polymeric surfactants wherein the weight ratio of hydrophobic solvent to non-polymeric surfactant is from about 30:1 to about 1:2; and one or more aqueous carriers; wherein the oral composition is in the form of a toothpaste or mouthrinse, is non-ingestible, and has a pH of from about 5.0 to about 9.5.

4 Claims, No Drawings

HYDROPHOBIC AGENTS AND NON-POLYMERIC SURFACTANTS USE IN ORAL CARE PRODUCTS

BACKGROUND OF THE INVENTION

The formation of dental plaque is the primary source of dental caries, gingival and periodontal disease, and tooth loss. Dental plaque is a mixed matrix of bacteria, epithelial cells, leukocytes, macrophages and other oral exudate. Bacteria comprise approximately three-quarters of the plaque matrix. Any given sample of dental plaque could contain as many a 400 different varieties of microorganisms. This mix includes both aerobic and anaerobic bacteria, fungi, and protozoa. Viruses have also been found in samples of dental plaque.

This matrix of organisms and oral exudate continues expanding and coalesces with other plaque growths situated nearby. The bacteria synthesize levans and glucans from sucrose found in the oral cavity providing energy for the microorganisms. These glucans, levans, and microorganisms form an adhesive skeleton for the continued proliferation of plaque.

Calculus is a yellow or white mineralized deposit of bacterial plaque. Inorganic in nature, calculus consists primarily of calcium and magnesium phosphate and calcium carbonate. Calculus forms in layers, as does plaque, and is simply the mineralization of plaque's layered bacteria. Calculus is formed when plaque's protein-carbohydrate matrix accumulates calcium followed by the precipitation and mineralization of crystalline calcium phosphate. Once mineralized calculus is formed, another layer of bacteria adheres to the surface forming yet another layer of plaque which is subsequently mineralized into calculus.

The failure to retard or stop the proliferation of plaque and calculus may be detrimental to oral health. Plaque and calculus formation may lead to dental caries, gingival inflammation, periodontal disease, and ultimately tooth loss.

The use of a variety of agents to clean the oral cavity and reduce plaque and calculus has been recognized for some time. Oral compositions containing solvents are known, for example U.S. Pat. No. 5,242,910, Sep. 7, 1993 to Damani; U.S. Pat. No. 5,192,532, Mar. 9, 1993 to Guay et al.; and U.S. Pat. No. 4,844,883, Jul. 4, 1989 to Patel. Although products containing solvents and other plaque and calculus reduction agents are known, there is a continuing need to develop improved products.

The present inventors have discovered that administration of the oral compositions of the present invention containing specific hydrophobic solvents and specific surfactants provides superior cleaning and abates the formation of plaque. Additionally, the solvents and surfactants are compatible in most oral compositions enabling much formula flexibility.

It is therefore an object of the present invention to provide oral compositions and a method of administering oral compositions comprising hydrophobic solvents and non-polymeric surfactants that are effective in arresting the accumulation of plaque. It is a further object of the present invention to provide such compositions and methods that will also abate subsequent calculus formation.

These objectives and additional objectives will become readily apparent from the detailed description which follows.

All percentages and ratios used herein are by weight, and all measurements are made at 25° C., unless otherwise specified.

SUMMARY OF THE INVENTION

The present invention relates to oral compositions and methods for reducing plaque in a human or lower animal subject comprising applying to the teeth of the subject an oral composition comprising one or more hydrophobic solvents having one or more characteristics selected from the group consisting of a hydrogen bonding parameter of less than about 7.0 and a water solubility of less than about 10%; one or more non-polymeric surfactants wherein the weight ratio of hydrophobic solvent to non-polymeric surfactant is from about 30:1 to about 1:2; and one or more aqueous carriers; wherein the oral composition is in the form of a toothpaste or mouthrinse, is non-ingestible, and has a pH of from about 5.0 to about 9.5.

DETAILED DESCRIPTION OF THE INVENTION

The oral composition of the present invention may be in the form of a toothpaste, mouth rinse, or liquid dentifrice. The term "toothpaste", as used herein, means paste, gel, or liquid formulations unless otherwise specified.

The term "oral composition" as used herein means a product which in the ordinary course of usage is not intentionally swallowed for purposes of systemic administration of particular therapeutic agents, but is rather retained in the oral cavity for a time sufficient to contact substantially all of the dental surfaces and/or oral tissues for purposes of oral activity. The oral composition is non-ingestible.

The term "aqueous carriers" as used herein means any safe and effective material for use in the compositions of the present invention. Such materials include thickening agents, humectants, water, buffering agents, abrasive polishing materials, titanium dioxide, alkali metal bicarbonate salts, peroxide source, flavor systems, xylitol, sweetening agents, coloring agents, and mixtures thereof.

The present compositions comprise several essential components, as well as optional components. The essential and optional components of the compositions of the present invention are described in the following paragraphs.

Hydrophobic Solvents

The method of treatment in the present invention includes applying to the teeth of the subject one or more hydrophobic solvents. The hydrophobic solvents may have a hydrogen bonding parameter of less than about 7.0, preferably less than about 6.5, and most preferred less than about 6.0. The hydrophobic solvents may also have a water solubility of less than 10%, preferably less than 7.5% and more preferably less than 5%. It is preferred that the hydrophobic solvent have the hydrogen bonding parameter characteristic and the water solubility characteristic. However, hydrophobic solvents having only one of the above characteristics are suitable. Suitable hydrophobic solvents for this invention include, but are not limited to, glyceryl triacetate, acetylated monoglyceride, benzyl benzoate, benzyl butyrate, benzyl phenyl acetate, butyl-2-decenoate, citronellyl butyrate, cresyl acetate, ethyl acetate, diethyl malonate, diethyl sebacate, triethyl citrate, diethyl succinate, glyceryl tributyrate, ethyl laurate, ethyl acetoacetate, diethyl tartrate, ethyl or butyl lactate, acetyl triethyl citrate, diethyl malate, ethyl oleate, sucrose octaacetate, benzyl alcohol, phenylethyl alcohol, diacetyl tartaric acid ester of mono and diglycerides, stearyl monoglyceridyl citrate, castor oil, succinylated monoglycerides, lactylic and glyceryl lacto ester of fatty acids, and combinations thereof. Preferred hydrophobic solvents include triacetin, diethyl malate, diethyl succinate, benzyl alcohol, phenylethyl alcohol, ethyl acetate, diethyl sebacate, ethyl acetoacetate, diethyl tartrate, butyl lactate, and ethyl lactate. The most preferred hydrophobic solvents are triacetin, diethyl malate, dietihyl succinate, benzyl alcohol, phenylethyl alcohol, and butyl lactate. One or more hydrophobic solvents will be administered in an amount of from about 0.5% to about 90%, preferably from about 1% to about 50%, more preferably from about 2% to about 10%, and most preferably from about 2% to about 6%, by weight of the composition.

Non-polymeric Surfactants

The present invention also includes administration of non-polymeric surfactants. Suitable non-polymeric surfactants are those which are reasonably stable and foam throughout a wide pH range. The non-polymeric surfactants may be anionic, select nonionic, amphoteric, zwitterionic, cationic, or mixtures thereof. Anionic surfactants useful herein include the water-soluble salts of alkyl sulfates having from 8 to 20 carbon atoms in the alkyl radical (e.g., sodium alkyl sulfate) and the water-soluble salts of sulfonated monoglycerides of fatty acids having from 8 to 20 carbon atoms. Sodium lauryl sulfate and sodium coconut monoglyceride sulfonates are examples of anionic surfactants of this type. Other suitable anionic surfactants are sarcosinates, such as sodium lauroyl sarcosinate, taurates, sodium lauryl sulfoacetate, sodium lauroyl isethionate, sodium laureth carboxylate, and sodium dodecyl benzenesulfonate. Mixtures of anionic surfactants can also be employed. Many suitable anionic surfactants are disclosed by Agricola et al., U.S. Pat. No. 3,959,458, issued May 25, 1976, incorporated herein in its entirety by reference. The select nonionic suitable for this invention include polyoxyethylene, polyoxyethylene sorbitan esters (sold under trade name Tweens), fatty alcohol ethoxylates, polyethylene oxide condensates of alkyl phenols, products derived from the condensation of ethylene oxide with the reaction product of propylene oxide and ethylene diamine, ethylene oxide condensates of aliphatic alcohols, long chain tertiary amine oxides, long chain tertiary phosphine oxides, long chain dialkyl sulfoxides, and mixtures of such materials. The amphoteric surfactants useful in the present invention can be broadly described as derivatives of aliphatic secondary and tertiary amines in which the aliphatic radical can be a straight chain or branched and wherein one of the aliphatic substituents contains from about 8 to about 18 carbon atoms and one contains an anionic water-solubilizing group, e.g., carboxylate, sulfonate, sulfate, phosphate, or phosphonate. Other suitable amphoteric surfactants are betaines, specifically cocamidopropyl betaine. Mixtures of amphoteric surfactants can also be employed. Many of these suitable nonionic and amphoteric surfactants are disclosed by Gieske et al., U.S. Pat. No. 4,051,234, issued Sep. 27, 1977, incorporated herein by reference in its entirety. The present composition typically administer one or more non-polymeric surfactants each at a level of from about 0.25% to about 12%, preferably from about 0.5% to about 8%, and most preferably from about 1% to about 6%, by weight of the composition.

The ratio of the hydrophobic solvent to the non-polymeric surfactant will be from about 30:1 to about 1:2, preferably from about 10:1 to about 1:1, and more preferably from about 5:1 to about 4:1.

Fluoride Ion Source

The present invention may also include administration of a soluble fluoride source capable of providing free fluoride ions. Preferred soluble fluoride ion sources include sodium fluoride, stannous fluoride, indium fluoride, and sodium monofluorophosphate. Sodium fluoride is the most preferred soluble fluoride ion source. Norris et al., U.S. Pat. No. 2,946.725, issued Jul. 26, 1960, and Widder et al., U.S. Pat. No. 3,678,154 issued Jul. 18, 1972, disclose such fluoride ion sources as well as others. Both patents are incorporated herein by reference in their entirety.

The present compositions will administer a soluble fluoride ion source capable of providing from about 50 ppm to about 3500 ppm, and preferably from about 500 ppm to about 3000 ppm of free fluoride ions.

Anticalculus Agents

The present invention may also include the application of oral compositions comprising an effective amount of an anticalculus agent. An effective amount, as used herein, is any amount of an anticalculus agent sufficient to be effective in reducing calcium phosphate mineral deposition related to calculus formation. The anticalculus agents include pyrophosphate salts such as the dialkali metal pyrophosphate salts, tetra alkali metal pyrophosphate salts, and mixtures thereof. Disodium dihydrogen pyrophosphate ($Na_2H_2P_2O_7$), tetrasodium pyrophosphate ($Na_4P_2O_7$), and tetrapotassium pyrophosphate ($K_4P_2O_7$) in their unhydrated as well as hydrated forms are the preferred species. In compositions of the present invention, the pyrophosphate salt may be present in one of three ways: predominately dissolved, predominately undissolved, or a mixture of dissolved and undissolved pyrophosphate.

Compositions comprising predominately dissolved pyrophosphate refer to compositions where at least one pyrophosphate ion source is in an amount sufficient to provide at least about 1.0% free pyrophosphate ions. The amount of free pyrophosphate ions may be from about 1% to about 15%, preferably from about 1.5% to about 10%, and most preferably from about 2% to about 6%, by weight of the composition. Free pyrophosphate ions may be present in a variety of protonated states depending on a the pH of the composition.

Compositions comprising predominately undissolved pyrophosphate as the anticalculus agent refer to compositions containing no more than about 20% of the total pyrophosphate salt dissolved in the composition, preferably less than about 10% of the total pyrophosphate dissolved in the composition. Tetrasodium pyrophosphate may be the anhydrous salt form or the decahydrate form, or any other species stable in solid form in the dentifrice compositions. The salt is in its solid particle form, which may be its crystalline and/or amorphous state, with the particle size of the salt preferably being small enough to be aesthetically acceptable and readily soluble during use. The amount of pyrophosphate salt useful in making these compositions is any tartar control effective amount, and is generally from about 1.5% to about 15%, preferably from about 2% to about 10%, and most preferably from about 2.5% to about 8%, by weight of the composition. Some or all of the tetrasodium pyrophosphate may be undissolved in the product and present as tetrasodium pyrophosphate particles. Pyrophosphate ions in different protonated states (e.g., $HP_2O_7^{-3}$) may also exist depending upon the pH of the composition and if part of the tetrasodium pyrophosphate is dissolved.

Compositions containing an anticalculus agent may also comprise a mixture of dissolved and undissolved pyrophosphate salts. Any of the above mentioned pyrophosphate salts may be used. The pyrophosphate salts are described in more detail in Kirk & Othmer, *Encyclopedia of Chemical Technology,* Fourth Edition, Volume 18, Wiley-lnterscience Publishers (1996), incorporated herein by reference in its entirety, including all references incorporated into Kirk & Othmer.

Other anticalculus agents to be used in place of or in combination with the pyrophosphate salt include such materials known to be effective in reducing calcium phosphate mineral deposition related to calculus formation. Agents included are synthetic anionic polymers [including polyacrylates and copolymers of maleic anhydride or acid and methyl vinyl ether (e.g., Gantrez), as described, for example, in U.S. Pat. No. 4,627,977, to Gaffar et al., the disclosure of which is incorporated herein by reference in its entirety; as well as, e.g., polyamino propane sulfonic acid (AMPS)], zinc citrate trihydrate, diphosphonates (e.g., EHDP; AHP), polypeptides (such as polyaspartic and polyglutamic acids), and mixtures thereof. Other anticalculus agents include polyphosphates. Polyphosphate is generally understood to consist of two or more phosphate molecules arranged primarily in a linear configuration, although some cyclic derivatives may be present. Inorganic polyphosphate salts include tetrapolyphosphate and hexametaphosphate, among others. Polyphosphates larger than tetrapolyphosphate usually occur as amorphous glassy materials, such as the polyphosphates manufactured by FMC Corporation which are commercially known as Sodaphos (n≈6), Hexaphos (n≈13), and Glass H (n≈21). The phosphate sources are described in more detail in Kirk & Othmer, *Encyclopedia of Chemical Technology,* Fourth Edition, Volume 18, Wiley-Interscience Publishers (1996), incorporated herein by reference in its entirety, including all references incorporated into Kirk & Othmer.

Aqueous Carriers

In preparing the present compositions, it is desirable to add one or more aqueous carrier materials to the compositions. Such materials are well known in the art and are readily chosen by one skilled in the art based on the physical and aesthetic properties desired for the compositions being prepared. Aqueous carriers typically be administered at a level of from about 10% to about 99.5%, preferably from about 50% to about 98%, and more preferably from about 85% to about 95%, by weight of the dentifrice composition.

The present invention compositions in the form of toothpastes, typically contain some thickening agents or binders to provide a desirable consistency. Preferred thickening agents are carboxyvinyl polymers, carrageenan, hydroxyethyl cellulose, and water soluble salts of cellulose ethers such as sodium carboxymethylcellulose and sodium carboxymethyl hydroxyethyl cellulose. Natural gums such as gum karaya, xanthan gum, gum arabic, and gum tragacanth can also be used. Colloidal magnesium aluminum silicate or finely divided silica can be used as part of the thickening agent to further improve texture. Thickening agents can be administered in an amount from about 0.1% to about 15%, by weight of the total composition.

Another optional component of the compositions desired herein is a humectant. The humectant serves to keep toothpaste compositions from hardening upon exposure to air and certain humectants can also impart desirable sweetness of flavor to toothpaste compositions. Suitable humectants for use in the invention include glycerin, sorbitol, xylitol, polyethylene glycol, propylene glycol, and other edible polyhydric alcohols. The humectant is generally administered in an amount of from about 0% to 70%, and preferably from about 15% to 55%, by weight of the compositions herein.

Water may be employed in the preparation of commercially suitable oral compositions. The water should preferably be of low ion content and free of organic impurities. Water generally comprises from about 5% to about 70%, and preferably from about 20% to about 50%, by weight of the composition herein. The amounts of water include the free water which is added plus that which is introduced with other materials, such as with sorbitol.

The oral composition may alternatively contain a very limited amount of water. A low water oral composition may be preferred for solvents that tend to hydrolyze, such as any hydrophobic solvent with an ester group. The low water oral compositions will generally have a water content of from about 1% to about 20% and preferably from about 5% to about 14%, by weight of the composition. The low water oral composition may be administered by itself or may be one composition in a dual department dentifrice dispenser. The dispenser may be a tube, pump, or any other container suitable for dispensing toothpaste. Dual compartment packages suitable for this purpose are described in U.S. Pat. No. 4,528,180, issued Jul. 9, 1985; U.S. Pat. No. 4,687,663, issued Aug. 18, 1987; and U.S. Pat. No. 4,849,213, issued Jul. 18, 1989, all to Shaeffer, all incorporated herein in their entirety. The dispenser will deliver approximately equal amounts of each dentifrice composition through an opening. The compositions may intermix once dispensed.

The pH of the present compositions is preferably adjusted through the use of buffering agents. Buffering agents, as used herein, refer to agents that can be used to adjust the pH of the compositions to a range of about pH 5.0 to about pH 9.5. Buffering agents include monosodium phosphate, trisodium phosphate, sodium hydroxide, sodium carbonate, sodium acid pyrophosphate, citric acid, and sodium citrate. Buffering agents can be administered at a level of from about 0.5% to about 10%, by weight of the present compositions.

An abrasive polishing material may also be included in the toothpaste compositions. The abrasive polishing material contemplated for use in the compositions of the present invention can be any material which does not excessively abrade dentin. These include, for example, silicas including gels and precipitates, calcium carbonate, dicalcium orthophosphate dihydrate, calcium pyrophosphate, tricalcium phosphate, calcium polymetaphosphate, insoluble sodium polymetaphosphate, hydrated alumina, and resinous abrasive materials such as particulate condensation products of urea and formaldehyde, and others such as disclosed by Cooley et al in U.S. Pat. No. 3,070, 510, issued Dec. 25, 1962, incorporated herein by reference. Mixtures of abrasives may also be used.

Silica dental abrasives of various types are preferred because of their unique benefits of exceptional dental cleaning and polishing performance without unduly abrading tooth enamel or dentine. The silica abrasive polishing materials herein, as well as other abrasives, generally have an average particle size ranging between about 0.1 to about 30 microns, and preferably from about 5 to about 15 microns. The abrasive can be precipitated silica or silica gels such as the silica xerogels described in Pader et al., U.S. Pat. No. 3,538,230, issued Mar. 2, 1970, and DiGiulio, U.S. Pat. No. 3,862,307, issued Jan. 21, 1975, both incorporated herein by reference. Preferred are the silica xerogels marketed under the trade name "Syloid" by the W. R. Grace & Company, Davison Chemical Division. Also preferred are the precipitated silica materials such as those marketed by the J. M. Huber Corporation under the trade name, "Zeodent", particularly the silica carrying the designation "Zeodent 119". The types of silica dental abrasives useful in the toothpastes of the present invention are described in more detail in Wason, U.S. Pat. No. 4,340,583, issued Jul. 29, 1982, and Rice, U.S. Pat. No. 5,589,160, issued Dec. 31, 1996, incorporated herein by reference. Silica abrasives described in U.S. patent application Ser. No. 08/434,147, filed May 2, 1995, are also herein incorporated by reference. The abrasive in the toothpaste compositions described herein is generally present at a level of from about 6% to about 70% by weight of the composition. Preferably, abrasives are generally administered at a level of from about 10% to about 50%, by weight of the composition.

Titanium dioxide may also be added to the present composition. Titanium dioxide is a white powder which adds pigment to the compositions. Generally, titanium dioxide is administered at a level of from about 0.25% to about 5%, by weight of the compositions.

The present invention may also include an alkali metal bicarbonate salt. Alkali metal bicarbonate salts are soluble in water and unless stabilized, tend to release carbon dioxide in an aqueous system. Sodium bicarbonate, also known as baking soda, is the preferred alkali metal bicarbonate salt. The alkali metal bicarbonate salt may be administered at a level of from about 0.5% to about 30%, preferably from about 0.5% to about 15%, and most preferably from about 0.5% to about 5% of the final composition.

A peroxide source may also be included. Preferred peroxide sources are calcium peroxide, aqueous hydrogen peroxide, cylium peroxide, and sodium peroxide. Peroxide is administered at a level of from about 1.0% to about 5.0%, by weight of the composition.

A flavor system can also be added to the compositions. Suitable flavoring components include oil of wintergreen, oil of peppermint, oil of spearmint, clove bud oil, menthol, anethole, methyl salicylate, eucalyptol, cassia, 1-menthyl acetate, sage, eugenol, parsley oil, oxanone, alpha-irisone, marjoram, lemon, orange, propenyl guaethol, cinnamon, vanillin, ethyl vanillin, heliotropine, 4-cis-heptenal, diacetyl, methyl-para-tert-butyl phenyl acetate, and mixtures thereof. Coolants may also be part of the flavor system. Preferred coolants in the present compositions are the para-menthan carboxyamide agents such as N-ethyl-p-menthan-3-carboxamide (known commercially as "WS-3") and mixtures thereof. A flavor system is generally administered at levels of from about 0.001% to about 5%, by weight of the composition.

The present invention may also include xylitol. Xylitol is a sugar alcohol that is used as a sweetener and humectant. Xylitol may provide a therapeutic effect, such as an antibacterial or anticaries effect. The present compositions typically administer xylitol at a level from about 0.01% to about 25%, preferably from about 3% to about 15%, more preferably from about 5% to about 12%, and most preferably from about 9% to about 11%, by weight of the total composition. Alternatively, if xylitol is used as a sweetener, it may be administered at a lower level, such as from about 0.005% to about 5%, by weight of the dentifrice composition.

Sweetening agents can be added to the compositions. These include saccharin, dextrose, sucrose, lactose, maltose, levulose, aspartame, sodium cyclamate, D-tryptophan, dihydrochalcones, acesulfame, and mixtures thereof. Various coloring agents may also be incorporated in the present invention. Sweetening agents and coloring agents are generally administered at levels of from about 0.005% to about 5%, by weight of the composition.

The present invention may also include other agents. Bis-biguanide antiplaque agents, such as chlorhexidine, can optionally be added to the compositions. The optional antiplaque agents generally are administered at a level of from about 0% to about 5%, by weight of the composition, so long as the free pyrophosphate ions are not hindered by the cationic active.

The present compositions can alternatively be in the form of a mouthrinse or liquid dentifrice where conventional mouthrinse components comprise the aqueous carriers of the present invention. Mouthrinses and liquid dentifrices generally comprise from about 20:1 to about 2:1 of a water ethyl alcohol or alcohol free solution, and preferably other ingredients such as flavors, sweeteners, preservatives, and humectants as those mentioned above. The humectants, such as glycerin and sorbitol, give a moist feel to the mouth. The preservatives, such as sodium benzoate and benzoic acid, help to lower the pH of the mouthrinse. Generally on a weight basis, the mouthrinses and liquid dentifrices of the present invention comprise from about 0% to about 60% ethyl alcohol, from about 0% to about 90% humectant, from about 0% to about 1% sweetening agent, from about 0% to about 2% flavoring agent, and the balance water. Alternatively, low water mouthrinse formulations may comprise higher amounts of humectants and lower amount of water. Other optional components described herein for use in toothpaste products are also useful in the mouthrinse and liquid dentifrice compositions.

The following examples further describe and demonstrate embodiments within the scope of the present invention. These examples are given solely for the purpose of illustration and are not to be construed as limitations of the present invention as many variations thereof are possible without departing from the spirit and scope. Other suitable solvents described in this specification may be substituted for the solvents included in the examples.

The present inventions relate to compositions and methods for reducing the incidence of plaque and/or calculus on dental enamel. The method of treatment herein comprises contacting the dental enamel surfaces in the mouth with the oral compositions according to the present invention. Generally, this is accomplished by brushing the teeth with one of the described compositions. Alternative methods, such as swishing a mouthrinse or toothpaste slurry with water in the mouth, may also be used. The oral compositions are non-ingestible.

For the purpose of illustration, Examples I–VII described below are utilized by a human or lower animal subject for reducing plaque and/or calculus by brushing, swishing, or by other administration means.

Toothpaste Examples

EXAMPLE I

| Ingredient | Weight % |
|---|---|
| Sorbitol$^{(a)}$ | 40.767 |
| Glycerin | 15.000 |
| Water | 12.340 |
| Sodium Fluoride | 0.243 |
| Sodium Saccharin | 0.400 |
| Monosodium Phosphate | 0.500 |
| Trisodium Phosphate | 1.500 |
| Xanthan Gum | 0.400 |
| Carbopol | 0.300 |
| Titanium Dioxide | 0.500 |
| Color Solution | 0.050 |
| Silica | 20.000 |
| Diethyl Succinate | 3.000 |
| Sodium Alkyl Sulfate$^{(c)}$ | 4.000 |
| Flavor System | 1.000 |

Example I is prepared as follows. Start by combining water and sorbitol. Mix thoroughly and add sodium fluoride, saccharin, and the phosphates. Next add the silica. Disperse the thickening agents, xanthan gum and carbopol, in the remaining humectant, glycerin, before adding to the mixture. Lastly, add the flavor system, diethyl succinate, color solution, titanium dioxide, and surfactant, sodium alkyl sulfate. Continue mixing until homogeneous. Mill and/or deareate the final product if desired for aesthetic preference.

EXAMPLE II

| Ingredient | Weight % |
| --- | --- |
| Sorbitol[a] | 28.240 |
| Glycerin | 10.000 |
| Water | 10.217 |
| Sodium Fluoride | 0.243 |
| Sodium Saccharin | 0.500 |
| Sodium Carbonate | 1.500 |
| Sodium Bicarbonate | 24.000 |
| Carboxymethylcellulose | 1.000 |
| Titanium Dioxide | 0.500 |
| Silica | 11.000 |
| Triacetin | 8.000 |
| Sodium Alkyl Sulfate[c] | 4.000 |
| Flavor System | 0.800 |

Example II is prepared as follows. Start by combining water and sorbitol. Mix thoroughly and add sodium fluoride and saccharin. Next add the sodium carbonate, sodium bicarbonate, and then the silica. Disperse the thickening agents, carboxymethylcellulose, in the remaining humectant, glycerin, before adding to the mixture. Lastly, add the flavor system, triacetin, titanium dioxide, and surfactant, sodium alkyl sulfate. Continue mixing until homogeneous. Mill and/or deareate the final product if desired for aesthetic preference.

EXAMPLE III

| Ingredient | Weight % |
| --- | --- |
| Sorbitol[a] | 16.611 |
| Glycerin | 10.000 |
| Water | 19.473 |
| Sodium Fluoride | 0.243 |
| Sodium Saccharin | 0.528 |
| Tetrasodium Pyrophosphate | 5.045 |
| Polyethylene Glycol 6 | 3.000 |
| Sodium Carbonate | 1.500 |
| Sodium Bicarbonate | 24.000 |
| Carboxymethylcellulose | 0.800 |
| Color Solution | 0.300 |
| Silica | 11.000 |
| Sodium Alkyl Sulfate[c] | 2.000 |
| Benzyl Alcohol | 4.000 |
| Flavor System | 1.500 |

Example III is prepared as follows. Start by combining water and sorbitol. Add sodium fluoride and saccharin. Add sodium carbonate. Next add the silica. The temperature of the mixture should be about 32° C. or less prior to the addition of sodium bicarbonate. Next, disperse the thickening agent, carboxymethylcellulose, in the remaining humectants, polyethylene glycol and glycerin, before adding to the mixture. Next add the flavor system, benzyl alcohol, color solution, and surfactant, sodium alkyl sulfate. Lastly, slowly add the tetrasodium pyrophosphate. Continue mixing until homogeneous. Mill and/or deareate the final product if desired for aesthetic preference.

EXAMPLE IV

| Ingredient | Wt. % |
| --- | --- |
| Carboxymethycellulose | 0.600 |
| Water | 7.000 |
| Flavor System | 1.000 |
| Glycerin | 30.440 |
| Cocoamidopropyl Betaine[d] | 5.000 |
| Propylene Glycol | 5.000 |
| Silica | 22.000 |
| Sodium Bicarbonate | 15.000 |
| Sodium Carbonate | 2.000 |
| Sodium Saccharin | 0.500 |
| Titanium Dioxide | 0.500 |
| Xanthan Gum | 0.200 |
| Triacetin | 7.000 |
| Polyethylene Glycol | 3.000 |
| Sodium Monofluorophosphate | 0.760 |

Example IV is prepared as follows. Add the water and saccharin to a mixing vessel. Disperse the thickening agents, carboxymethyl cellulose and xanthan gum, in the glycerin. Add this mixture of dispersed thickening agents in glycerin to the mixing vessel, mix well, and heat to at least 40° C. Mix the flavor, triacetin, and cocoamidopropyl betaine and add to the mixture. Add the polyethylene glycol, propylene glycol, and sodium carbonate. Mix well. Next, add the titanium dioxide and the silica. After mixing, add the sodium bicarbonate and sodium monofluorophosphate. Continue stirring the mixture until homogeneous.

EXAMPLE V

| Ingredient | Weight % |
| --- | --- |
| Glycerin | 25.050 |
| Polyethylene Glycol 12 | 2.000 |
| Xanthan Gum | 0.300 |
| Carboxymethylcellulose | 0.200 |
| Water | 5.000 |
| Sodium Saccharin | 0.450 |
| Sodium Fluoride | 0.243 |
| Xylitol | 10.000 |
| Sodium Lauroyl Sarcosinate | 2.000 |
| Cocamidopropyl Betaine[d] | 2.000 |
| Triacetin | 6.000 |
| Sodium Carbonate | 2.600 |
| Titanium Dioxide | 1.000 |
| Silica | 20.000 |
| Sodium Bicarbonate | 1.500 |
| Propylene Glycol | 15.011 |
| Tetrasodium Pyrophosphate | 5.046 |
| Calcium Peroxide | 0.500 |
| Flavor System | 1.100 |

Example V is prepared as follows: Add approximately half of the glycerin to a mixing vessel. Disperse the thickening agents, carboxymethyl cellulose and xanthan gum, in the humectants, polyethylene glycol and propylene glycol. Add this mixture of dispersed thickening agent in humectant to the mixing vessel. Dissolve the sodium fluoride and sodium saccharin in water and add to the mixture. Add the xylitol and cocamidopropyl betaine. The flavor system, triacetin, and sodium lauroly sarcosinate are then added. Next, add the sodium carbonate, titanium dioxide, and the silica. Add the sodium bicarbonate. Disperse the tetrasodium pyrophosphate in the remaining glycerin and add to the mixture. Finally, add the calcium peroxide. Stir the mixture until homogeneous and then heat the mixture to a temperature range of from about 110° F. to about 160° F. This temperature should be maintained for about 30–60 minutes. Finally, the mixture may be cooled and deaerated.

EXAMPLE VI

| Ingredient | Weight % |
| --- | --- |
| Glycerin | 53.000 |
| Polyethylene Glycol 32 | 8.500 |
| Polyethylene Glycol 6 | 18.000 |
| Carboxymethylcellulose | 4.000 |
| Sodium Saccharin | 0.500 |
| Triacetin | 10.000 |
| Sodium Alkyl Sulfate[c] | 5.000 |
| Flavor System | 1.000 |

Example VI is prepared as follows: Add glycerin and triacetin. Add both polyethylene glycols, carboxymethylcellulose, and sodium alkyl sulfate and mix well. Add flavor and saccharin and continuing mixing until homogenous.

Mouthrinse Example

EXAMPLE VII

| Ingredient | Weight % |
| --- | --- |
| Glycerin | 10.000 |
| Propylene Glycol | 62.459 |
| Sorbitol[a] | 20.000 |
| Sodium Benzoate | 0.320 |
| Benzoic Acid | 0.021 |
| Sodium Saccharin | 0.700 |
| Triacetin | 4.000 |
| Sodium Alkyl Sulfate[c] | 1.000 |
| Flavor System | 1.500 |

Example VII is prepared as follows: Add propylene glycol and triacetin. Next add the flavor, benzoic acid, glycerin, sorbitol, and sodium alkyl sulfate. Finally add the sodium benzoate and sodium saccharin and mix until homogeneous.

(a) 70% solution of sorbitol in water
(b) 60% solution of tetrapotassium pyrophosphate in water
(c) 27.9% solution of sodium alkyl sulfate in water
(d) 30% solution of cocoamidopropyl betaine in water

What is claimed is:

1. A method for reducing and abating formation of plaque in a human or lower animal subject comprising applying to the teeth of the subject an oral composition comprising:

a. one or more hydrophobic solvents having one or more characteristics selected from the group consisting of a hydrogen bonding parameter of less than about 7.0 and a water solubility of less than about 10%;

b. one or more non-polymeric surfactants wherein the weight ratio of hydrophobic solvent to non-polymeric surfactant is from about 30:1 to about 1:2; and c. one or more aqueous carriers;

wherein the oral composition is in the form of a toothpaste or mouthrinse, is non-ingestible, and has a pH of from about 5.0 to about 9.5, and wherein the hydrophobic solvent is the essential agent for abating the formation of plaque.

2. The method according to claim 1 wherein the hydrophobic solvent is in an amount of from about 0.5% to about 90% and is selected from the group consisting of triacetin, diethyl malate, diethyl succinate, benzyl alcohol, phenylethyl alcohol, ethyl acetate, diethyl sebacate, ethyl acetoacetate, diethyl tartrate, butyl lactate, ethyl lactate, and combinations thereof.

3. The method according to claim 2 wherein each of the one or more non-polymeric surfactants is in an amount of from about 0.25% to about 12% and are selected from the group consisting of anionic surfactants, select nonionic surfactants, amphoteric surfactants, zwitterionic surfactants, cationic surfactants, and mixtures thereof.

4. The method according to claim 3 further comprising a fluoride ion source capable of providing from about 50 ppm to about 3500 ppm of free fluoride ions and wherein the fluoride ion source is selected from the group consisting of sodium fluoride, stannous fluoride, sodium monofluorophosphate, potassium fluoride, and mixtures thereof.

* * * * *